United States Patent [19]

Wagner et al.

[11] Patent Number: 5,449,791

[45] Date of Patent: * Sep. 12, 1995

[54] PROCESS FOR THE PREPARATION OF PROPYLENE GLYCOL CARBONATE

[75] Inventors: Paul Wagner, Düsseldorf; Christine Mendoza-Frohn, Erkrath; Hans-Josef Buysch, Krefeld, all of Germany

[73] Assignee: Bayer Aktiengesellschaft, Leverkusen, Germany

[ * ] Notice: The portion of the term of this patent subsequent to Sep. 27, 2011 has been disclaimed.

[21] Appl. No.: 251,456

[22] Filed: May 31, 1994

[30] Foreign Application Priority Data

Jun. 7, 1993 [DE] Germany ................. 43 18 892.3

[51] Int. Cl.$^6$ ................. C07D 317/36; C07D 317/38
[52] U.S. Cl. ................. 549/230; 549/228; 549/229
[58] Field of Search ................. 549/228, 229, 230

[56] References Cited

U.S. PATENT DOCUMENTS

| | | | |
|---|---|---|---|
| 4,247,465 | 1/1981 | Kao et al. | 549/230 |
| 4,314,945 | 2/1982 | McMullen et al. | 549/228 |
| 4,851,570 | 7/1989 | Zaby et al. | 560/347 |
| 5,281,723 | 1/1994 | Bantu et al. | 549/229 |
| 5,350,862 | 9/1994 | Wagner et al. | 549/230 |

FOREIGN PATENT DOCUMENTS

| | | | |
|---|---|---|---|
| 546428 | 12/1992 | European Pat. Off. | |
| 202022 | 8/1993 | Japan | 549/229 |
| 172342 | 6/1965 | U.S.S.R. | |
| 4340 | 3/1992 | WIPO | 549/228 |

OTHER PUBLICATIONS

Zaby et al, Chem. Abst. 112:78154d (1990).
Patent Abstracts of Japan, vol. 6, No. 197, 1982 and JP-A-57 106 631, Jul. 1982.
Chemie-Ingenieur-Techn., vol. 43, No. 16, Jan. 1971, pp. 903-905; "Äthylenund Propylencarbonat", G. Hechler.
Fette-Seifen-Anstrichmittel, 1971, vol. 73, No. 6, pp. 396-399; "Die technishce Herstellung von Äthylencarbonat", H. Springmann.

Primary Examiner—Cecilia Tsang
Attorney, Agent, or Firm—Sprung Horn Kramer & Woods

[57] ABSTRACT

A process is described for the catalytic preparation of propylene glycol carbonate (PGC) by reacting propylene oxide (POX) and $CO_2$ in PGC as reaction medium at elevated temperature and elevated pressure and separating off from the catalyst the PGC formed. The process is carried out continuously under adiabatic temperature conditions. Per unit of time, PGC as reaction medium flows into the reactor at 7 to 350 times the amount of the PGC formed per unit of time. At all points of the reactor a $CO_2$ excess is maintained over the other reaction partner POX. Of the effluent reaction mixture, 80 to 98% by weight are returned to the entrance of the reactor, while the remainder is worked up to give PGC. The sensible heat of the reaction product resulting from the adiabatic temperature conditions can be used for the work-up.

20 Claims, 1 Drawing Sheet

PROCESS FOR THE PREPARATION OF PROPYLENE GLYCOL CARBONATE

BACKGROUND OF THE INVENTION

1. Field of the Invention

The present invention relates to a process for the continuous catalytic preparation of propylene glycol carbonate (PGC) from propylene oxide (POX) and carbon dioxide ($CO_2$), which is characterized by an adiabatic and particularly mild, energy- and material-saving procedure.

2. Description of the Related Art

Many proposals have been made for the preparation of PGC. These primarily relate to the use of certain catalysts. A process for the preparation of PGC or ethylene glycol carbonate (EGC) from POX or ethylene oxide (EOX), respectively, and $CO_2$ is described in Chem. Ing. Techn. 43 (1971), 903. This process also underlies the publication in Fette, Setfen, Anstrichmittel 73, (1971), 396, but here, only the preparation of EGC is specifically considered. For the preparation of EGC, adiabatic temperature conditions are considered there to be technically not realizable (loc. cit. 398). In the process described there, $CO_2$, and EOX are reacted together at 80 bar and 190° to above 200° C. in a reactor filled with ethylene glycol carbonate and the heat of reaction is removed with the aid of a heat transport medium circulating in counter-current, which in turn is cooled with water. Under such reaction conditions peak temperatures up to 220° C. in the reactor are obtained which have a product-damaging action, which is explicitly referred to in the cited publication (p. 397), and which would be difficult to master in particular in the case of industrial plants. The entire energy of reaction is removed unused in this case. Since the reaction of POX with $CO_2$ to give PGC has a similarly high heat of reaction as that of EOX with $CO_2$ to give EGC and temperature peaks likewise act in a product-damaging way on the PGC, the statements from Fette, Seifen (loc. cit.) can also be applied to the preparation of PGC from POX and $CO_2$, Adiabatic temperature conditions, in contrast to the procedure described in Fette, Seifen (loc. cit.) and Chem. Ing. Techn. (loc. cit.), are characterized in that the entire heat of reaction liberated is absorbed by the reaction mixture itself; in the case of exothermic reactions this leads to an increase in the temperature of the reaction mixture.

In the process which is described in U.S. Pat. No. 4,314,945, the reactors for the preparation of alkylene carbonates from alkylene oxides and $CO_2$, take as a basis various combinations of flow tubes and pumped circulation reactors which are operated at 10–50 bar and 100 to a maximum of 200° C. The corresponding carbonate serves in all reactor parts as reaction medium and there makes up in each case 85–99.6% by weight of the reactor contents.

The alkylene oxide is metered into the first reaction zone of such a combination jointly with the catalyst dissolved in the carbonate.

The feeding of the $CO_2$, is carried out in the combination preferred in U.S. Pat. No. 4,314,945 of a pumped circulation reactor with downstream flow tubes at a different, remote point of the reactor. Precisely in the first reactor of such a combination, where the local alkylene oxide concentration is still particularly high in the immediate surroundings of the metering site, the type of metering selected acts disadvantageously on the selectivity: the alkylene oxide, promoted by the high local catalyst concentration and the lower $CO_2$ concentration, can rearrange to form acetaldehyde and thus serves as a base for polycondensation reactions. It is disadvantageous, moreover, that $CO_2$ is only fed in a slight excess with respect to the catalyst (and not with respect to the alkylene oxide). The components for the combinations, which represent a reactor, used in U.S. Pat. No. 4,314,945 are on the one hand pumped circulation reactors—comprising a stirred tank stirred by a stirrer or by the gas or liquid flowing in, having an external circulation and heat exchanger for product cooling—and on the other hand flow tubes operated under adiabatic temperature conditions and with a subsequent cooler or themselves provided with a cooler.

A pumped circulation reactor is characterized in that high pumped circulation rates are employed in the case of exothermic reactions, the heat of reaction being removed during the reaction in the reactor and in the associated heat exchanger. This procedure is completely different from the adiabatic technique in which the reaction is completed in one pass through the reactor and the entire heat of reaction is absorbed by the reaction medium.

Common to the reactor components in U.S. Pat. No. 4,314,945 is that, independently of their number and sequence within the combination, in each of them only a partial conversion of the alkylene oxide can take place since otherwise the heat problem of the highly exothermic reaction of the alkylene oxide with the $CO_2$ is not mastered.

Only by a complex connection of these individual components, each furnished with coolers, with partial conversion can, in total, a conversion rate of alkylene oxide of at least about 99.5% and a carbonate selectivity of at least about 99% be achieved.

Use of the sensible heat of the reaction in the process itself or for producing steam is not described in U.S. Pat. No. 4,314,945.

There was the desire to develop a process which on the one hand avoids damaging temperature peaks and on the other hand uses the energy of reaction as far as possible; such a use can proceed in the context of the process according to the invention itself, for example for working up the crude product or for generating heating steam for other processes.

SUMMARY OF THE INVENTION

A process has been found for the catalytic preparation of propylene glycol carbonate (PGC) by reacting propylene oxide (POX) and carbon dioxide in PGC as reaction medium at elevated temperature and elevated pressure and separating off from the catalyst the PGC formed, which is characterized in that a) the process is carried out continuously and adiabatically at a pressure of 2 to 200 bar, preferably 5 to 80 bar, particularly preferably 8 to 60 bar and within a temperature range of 110° to 200° C., preferably 110° to 190° C., particularly preferably 110° to 180° C. with an adiabatic temperature increase of 2° to 80° C., the entry temperature being selected so that the adiabatic temperature increase remains within the temperature range mentioned, b) the PGC flowing into the reactor as reaction medium per unit of time is 7 to 350 times the PGC formed in this unit of time, c) 1.01 to 1.5 mol, preferably 1.01 to 1.4 mol, particularly preferably 1.01 to 1.35 mol of carbon dioxide are used per mole of POX and at all points of the reactor a carbon dioxide excess is maintained and d) 80 to 98% by weight, preferably 85 to 97% by weight, of the total reaction mixture are returned to the entrance of the reactor and the remainder is worked up to give PGC.

BRIEF DESCRIPTION OF THE DRAWING

The accompanying

DETAILED DESCRIPTION OF THE INVENTION

Figure 1:
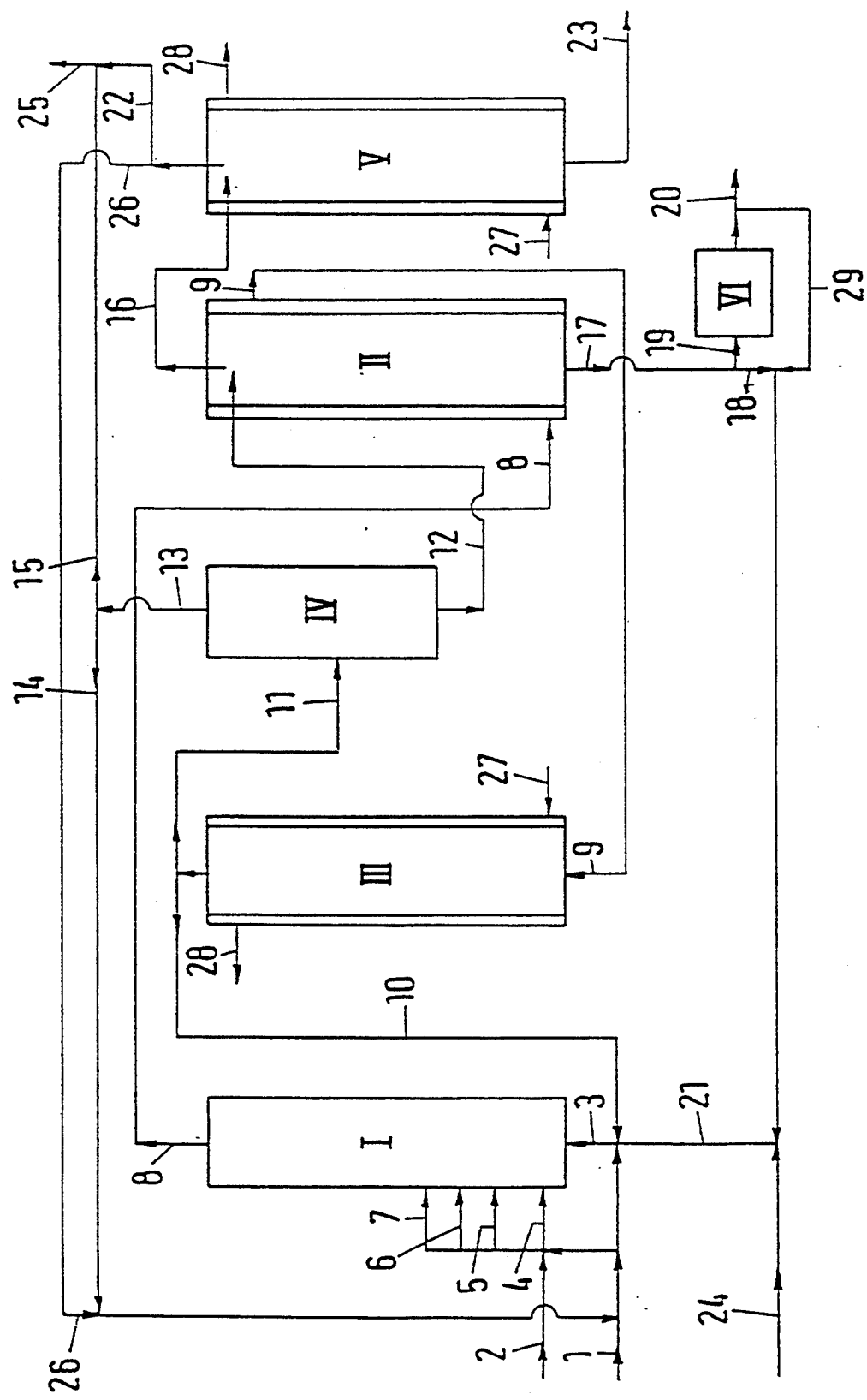
FIG. 1 shows an exemplary performance of the inventive process with the reactor (I), a flash evaporator (II), a heat exchanger (III), an expansion vessel (IV), a further heat exchanger (V), and a catalyst regeneration (VI). Further details will be given below.

The feedstocks POX and $CO_2$ are generally used in a purity of at least 99%. However, it is equally possible to use POX and $CO_2$ in a lower purity if the remainder up to 100% is composed of inert materials such as hydrocarbons, carbon monoxide or nitrogen. This applies particularly to $CO_2$ which can originate from various sources, for example from natural sources or from plants for generating water gas, carbon monoxide or reformers and is accordingly of lower purity. However, such inert gases are expediently present at a proportion of no more than 10% by volume, preferably no more than 5% by volume, particularly preferably no more than 3% by volume.

The catalysts used are virtually all those previously proposed, such as alkali metal bromides and alkaline earth metal bromides and alkali metal iodides and alkaline earth metal iodides, guanidines and hydrobromides or hydroiodides thereof, tetraalkylammonium bromides and tetraalkylammonium iodides, phosphonium bromides and phosphonium iodides, pyridinium halides, sulphonium halides, stibonium halides and arsonium halides, zinc halides and lead halides, alkyltin compounds or mixtures of alkali metal halides with halides of divalent metal ions (FR 1 538 576; BE 872 960; EP 297 647; U.S. Pat. Nos. 3,535,342; 2,773,070; 2,994,705; DE 15 43 555; U.S. Pat. No. 3,535,41; BE 798 171; BE 872 959; German Offenlegungsschrift 32 44 456; GB 2 098 985; EP 133 763; EP 180 387; J. Org. Chem. 45 (1980), 3735; Chem. Lett. 1979, 573; German Offenlegungsschrift 41 05 554). The catalysts preferably used are: alkali metal bromides and alkali metal iodides, tetraalkylammonium bromides and tetraalkylammonium iodides, phosphonium halides, guanidinium halides and mixtures of alkali metal halides with halides of divalent metals.

The process is carried out in the temperature range of 110° to 200° C., preferably 110° to 190° C., particularly preferably 110° to 180° C. The pressure for the process according to the invention is 2 to 200 bar, preferably 5 to 80 bar, particularly preferably 8 to 60 bar; at temperatures in the upper part of the range given, pressures also in the upper part of the range given are used and vice versa.

The process according to the invention is carried out under adiabatic temperature conditions, so that the adiabatic temperature increase is 2° to 80° C. The entry temperature is selected in this case so that even with complete utilization of the adiabatic temperature increase selected, the upper limit of the given temperature range for the entire process is not exceeded.

According to the invention, at all points of the reactor a $CO_2$ excess is maintained over the other reaction partner POX. For this purpose, 1.01 to 1.5 mol, preferably 1.01 to 1.4 mol, particularly preferably 1.01 to 1.35 mol of $CO_2$ are used per mole of POX.

PGC as reaction medium is always present in a great excess over the newly formed PGC. Thus, per unit of time, 7 to 350 times the PGC formed in this unit of time flows to the reactor as circulation PGC which also contains the catalyst. This great excess is further maintained in that 80 to 98% by weight, preferably 85 to 97% by weight, of the total reaction mixture are returned to the entrance of the reactor and only the remainder up to 100% is taken off and worked up to give pure PGC.

It is a further characteristic of the process according to the invention that the sensible heat of the reaction mixture, resulting from the adiabatic temperature conditions, is used. The most important of these possible uses is in this case that for working up the reaction mixture to give pure PGC. However, the sensible heat of the reaction product achieved is generally so high that, moreover, heating steam can still be generated which can be fed to other (endothermic) processes. Preferably, to recover the sensible heat, a cooling of the reaction mixture by 2° to 80° C. is performed in this case.

To avoid undesirable temperature peaks, intensive mixing is maintained in the reactor.

Further details of the process according to the invention are described below, for which, moreover, reference is made to the accompanying FIG. 1, which shows by way of example a possible embodiment of the process according to the invention. The work-up of the reaction mixture is carried out by distillation in this example. Obviously, other embodiment variants than that of FIG. 1 are possible.

The reactor (I) is a well insulated apparatus, for example a well insulated tubular reactor; it contains internals which ensure a continuous good distribution of the added gases POX and $CO_2$, and produce intensive mixing at all points. Such internals which are known to those skilled in the art are for example perforated plates, perforated trays and baffle trays, pipe distributors (insert and annular distributors), two-component nozzles, jet nozzles, nozzle trays, nozzles, particularly those according to German Offenlegungsschrift 37 36 988 and German Offenlegungsschrift 37 44 001, industrially conventional gas-introduction trays, sintered metal frits, closed gas distributor trays having through holes for the PGC, rotating gas-introduction apparatuses, impingement aerator elements (Perrys Chemical Engineers' Handbook 1984 pp. 18.57–18.70), mixer elements, metal sheet internals for increasing the turbulence, segmental and annular baffles. These internals can also be used in combination with each other. Generally, such internals, apart from good mixing of the flow (macromixing) and the fine gas distribution, should generate as large a proportion as possible of high-frequency turbulence elements in the dissipation area. Preferred internals are perforated trays, pipe distributors, two-component nozzles, jet nozzles, nozzles, particularly those according to German Offenlegungsschrift 37 36 988 and German Offenlegungsschrift 37 44 001, closed gas distributors, impingement aerator elements and mixer elements.

$CO_2$, in the process according to the invention, according to embodiment variant of FIG. 1, is fed in at (1)

and POX is fed in at (2). Since it is of importance for the high selectivity of the reaction according to the invention that POX encounters $CO_2$, everywhere in the reactor and itself occurs nowhere in excess or even only in high concentrations, $CO_2$ is fed into the reactor before the POX in the direction of flow. This feeding of $CO_2$ performed before the POX is carried out at least in part, while the remainder of $CO_2$ is fed in one or more part-quantities at other points of the reactor so that $CO_2$ is always present in excess over the POX. In a preferred variant, according to FIG. 1, $CO_2$ is added completely or at least partially to the PGC (3), which already contains the catalyst, flowing into the reactor even before entry into the reactor. Preferably, this advance addition of $CO_2$, is the excess of $CO_2$ in the scope of the abovedescribed $CO_2$ excess over the amount of the POX of 1 to 50 mol %. POX is only added at a later entry point (4), preferably in a mixture with $CO_2$; such a mixture is composed in a particularly preferred manner of equimolar amounts of POX and $CO_2$. In a further preferred manner, a POX/$CO_2$ mixture is fed into the reactor at at least two feed points. Such an at least second feed point is (5), other feed points can be (6) and (7) and still others. These gases fed in are then distributed uniformly in the reaction medium with the aid of the abovementioned internals (distribution elements). The greater number of the feed points (4), (5), (6), (7) and others avoids local overconcentrations and local temperature peaks in the reactor.

After the main reaction has decayed in the reactor (I), the reaction mixture (8), for utilization of the sensible heat, flows into the heating jacket of the flash evaporator (II) and from there flows as cooled reaction mixture (9) for further utilization by a heat exchanger (III) in which heating steam (28) is obtained from water (27). However, the efflux (8) of the reactor can alternatively be first conducted through the heat exchanger (III) and then through the heating jacket of the flash evaporator (II). A reactor to be heated of a completely different process, the reaction of which proceeds endothermically, can alternatively replace the heat exchanger (III) generating heating steam. However, the efflux (8), even before entry into the flash evaporator (II), can be divided into part-streams, corresponding to (10) and (11).

For the reactor efflux (8) and the reaction mixture (9) already somewhat cooled, the passes through (II) and (III) at the same time represent a time period serving for the postreaction.

The still further cooled reaction mixture, leaving the heat exchanger (III) in the example of FIG. 1, the sensible heat of which has decreased in total by the abovementioned amount of 2° to 80° C., is then divided into the part-streams (10) and (11). The pan-stream (10) includes in the manner already described above 80 to 98% by weight of the total efflux of reactor (I); the part-stream (11) represents the remainder up to 100%. Obviously, it is possible in principle to carry out the division (9) into the part-streams (10) and (11) at another point of the process course.

Whereas the part-stream (10) is returned to the reactor entrance, the part-stream (11) is fed to work-up. For this purpose (11) is first passed into an expansion vessel (IV), in which a separation into liquid (12) and a gas phase (13) proceeds. The gas phase (13) contains excess $CO_2$, possibly incompletely reacted POX and any inert gases introduced with the $CO_2$ and the POX. Depending on the proportion of inert gases, the gas phase (13) is divided into the two part-streams (14) and (15). (14) is returned to the reactor, while (15) is fed to the waste gas disposal (25). Clearly, with higher inert gas contents, a higher proportion of (13) is ejected in the form of the part-stream (15) and vice versa; simple analytical determinations and calculations and preliminary trials give for those skilled in the art without difficulty the optimum of the division of the gas phase (13).

The liquid (12) separated off in (IV) is then passed into the interior of the flash evaporator (II). The flash evaporator (II) is preferably a thin film evaporator, a falling film evaporator, a rotary tube evaporator or a rotary or ascending film evaporator. In (II), a separation by distillation into vaporized PGC (16) and a liquid bottom efflux (17) is performed at a vacuum of 2 to 100 mbar, preferably 4 to 90 mbar, particularly preferably 5 to 80 mbar. The energy for this separation by distillation can originate on the one hand from the reactor efflux (8), which is passed through the jacket or other heating device of the flash evaporator (II), and on the other hand from the further inherent sensible heat of the liquid phase (12).

The bottom efflux (17) of (II) is divided into the part-streams (18) and (19). The majority by far, for example 60 to 98%, preferably 75 to 97%, particularly preferably 90 to 96%, of the total amount of (17) returns to the reactor entrance as part-stream (18).

It still contains the catalyst. This, moreover, closes the circulation of the PGC serving as reaction medium circulated in the reactor system.

The remaining part-stream (19) flows to a regeneration facility (VI) for the catalyst. The type of regeneration of the catalyst must be specifically tailored to the individual catalyst used and is known to those skilled in the art, if a regeneration of the catalyst is possible at all, from the abovementioned literature. From the regeneration (VI), a fraction of catalyst (20) which has become, for example, inactive, can be discharged. The regenerated catalyst in the mixture with PGC (29) is returned to the reactor entrance just as the part-stream (18). The regeneration can be carried out, for example, so that catalysts of the type of mixtures of alkali metal halides with halides of divalent metals, for example NaBr/$ZnBr_2$, are treated with halogen compounds, for example HBr.

A supplementation of exhausted and discharged catalyst by fresh catalyst (24) passes into the reactor via (21).

The PGC (16) distilled off leaving the interior of (II) is condensed in a further heat exchanger (V) with recovery of vapour and cooled to the desired temperature. Such a condensed PGC is taken off at (23).

Any gaseous portions of (12), which were brought to (V) together with vaporized (16), are produced in (V) in the condensation of PGC as a gaseous stream to be withdrawn overhead, which is divided into the two part-streams (22) and (26). (22) is fed to the waste gas disposal (25), while (26) is returned to the reactor entrance. The division into the part-streams (22) and (26) takes place with the application of similar criteria as has already been described further above for the part-streams (14) and (15).

(27) is the water fed to the heat exchangers (III) and (0, which can be taken off from these apparatuses by utilization of the heat of evaporation or sensible heat as heating steam (28) produced.

Example

Into the reactor I according to FIG. 1, operated at 15 bar, there are metered in per hour in total via (1) 0.453 kg of $CO_2$ and via (2) 0.569 kg of POX, that is to say in such a way that 0.108 kg of $CO_2$ and 0.142 kg of POX flow as a mixture through each of the lines (4) to (7) and 0.022 kg of $CO_2$ is added (3) to the reaction mixture of about 30.2 kg returning via (10) having a temperature of approximately 141° C. before entry into the reactor I. A further 0.03 kg of gas flows from the expansion IV via (13) and (14) to the reactor I.

After the course of the reaction, 31.8 kg of reaction mixture having a temperature of approximately 159° C. leave the reactor and flow as stream (8) into the jacket of the flash evaporator II, which they leave at about 150° C. after heating the distillation occurring therein, and flow as stream (9) into the heat exchanger III, which they leave at about 150° C. after generating steam, and then are divided into the stream (10) of approximately 30.2 kg and (11) of approximately 1.6 kg. (10) returns, as described, into the reactor, while (11) is depressurized in IV to 1 bar, the gaseous phase (13) of 0.03 kg being passed to I and the liquid phase (12) of 1.57 kg being passed to the flash evaporator II and there, at about 50 mbar, being split into approximately 1.03 kg of vaporous PGC (16) and approximately 0.54 kg of bottom product (17). The residual gas of about 0.03 kg escaping in this case is taken off via (22) and (25) to the waste gas disposal. PGC (16) condenses in the heat exchanger V with steam generation.

After division of the bottom product (17) equivalent to approximately 9:1, the greater amount of approximately 0.49 kg flows as stream (18) and (21) to I and the smaller amount of approximately 0.05 kg (19) flows into the regeneration VI, which, after treatment with a very low amount of a halogen compound, it leaves again as (29) and is returned as (21) to the reactor.

What is claimed is:

1. A process for the catalytic preparation of propylene glycol carbonate (PGC) by reacting propylene oxide (POX) and carbon dioxide in PGC as reaction medium at elevated temperature and elevated pressure and separating off from the catalyst the PGC formed, wherein
   a) the process is carried out continuously and adiabatically at a pressure of 2 to 200 bar and within a temperature range of 110° to 200° C. with an adiabatic temperature increase of 2° to 80° C., the entry temperature being selected so that the adiabatic temperature increase remains within the temperature range mentioned,
   b) the PGC flowing into the reactor as reaction medium per unit of time is 7 to 350 times the PGC formed in this unit of time,
   c) 1.01 to 1.5 mol of carbon dioxide are used per mole of POX and at all points of the reactor a carbon dioxide excess is maintained and
   d) 80 to 98% by weight of the total reaction mixture are returned to the entrance of the reactor and the remainder is worked up to give PGC.

2. The process of claim 1, wherein the pressure range is 5 to 80 bar.

3. The process of claim 2, wherein the pressure range is 8 to 60 bar.

4. The process of claim 1, wherein the temperature range is 110° to 190° C.

5. The process of claim 4, wherein the temperature range is 110° to 180° C.

6. The process of claim 1, wherein 1.01 to 1.4 mol of carbon dioxide are used per mole of POX.

7. The process of claim 6, wherein 1.01 to 1.35 mol of carbon dioxide are used per mole of POX.

8. The process of claim 1, wherein intensive mixing is maintained in the reactor.

9. The process of claim 8, wherein the reactor contains perforated trays, pipe distributors, two-component nozzles, jet nozzles, nozzles, closed gas distributors, impingement aerator elements, mixer elements or a combination of a plurality thereof.

10. The process of claim 1, wherein, to generate the carbon dioxide excess, at least some of the carbon dioxide is fed into the PGC serving as reaction medium before the injection of the POX.

11. The process of claim 10, wherein the carbon dioxide fed before the injection of the POX is added to the PGC before entry into the reactor.

12. The process of claim 10, wherein POX, alone or as a mixture with any remaining carbon dioxide, is fed into the reactor at at least two sequentially following points in such a way that a carbon dioxide excess always exists.

13. The process of claim 12, wherein the excess of carbon dioxide provided is added to the PGC before its entry into the reactor and the remaining carbon dioxide is fed into the reactor as an equimolar $POX/CO_2$ mixture.

14. The process of claim 1, wherein the sensible heat achieved of the reaction mixture is used for the work-up of the reaction mixture to give PGC and/or is used in the generation of heating steam and/or is used in carrying out endothermic processes.

15. The process of claim 14, wherein in the recovery of the sensible heat, a cooling of the reaction mixture by 2° to 80° C. takes place.

16. The process of claim 14, wherein the work-up to give PGC is carried out with utilization of the recovered sensible heat.

17. The process of claim 16, wherein the work-up is carried out by distillation at 2 to 100 mbar.

18. The process of claim 17, wherein distillation is carried out at 4 to 90 mbar.

19. The process of claim 18, wherein distillation is carried out at 5 to 80 mbar.

20. The process of claim 1, wherein according to step d) 85 to 97% by weight of the total reaction mixture are returned to the entrance of the reactor.

* * * * *